(12) United States Patent
Fukui et al.

(10) Patent No.: US 9,237,996 B2
(45) Date of Patent: Jan. 19, 2016

(54) GLUCOSYLTRANSFERASE INHIBITOR CONTAINING EPIGALLOCATECHIN GALLATE POLYMER AS ACTIVE INGREDIENT

(75) Inventors: Yuko Fukui, Mishima-gun (JP); Michiyo Nakano, Suita (JP); Takashi Ooshima, Suita (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 0 days.

(21) Appl. No.: 13/061,073

(22) PCT Filed: Aug. 14, 2009

(86) PCT No.: PCT/JP2009/064335
§ 371 (c)(1),
(2), (4) Date: Feb. 25, 2011

(87) PCT Pub. No.: WO2010/024138
PCT Pub. Date: Mar. 4, 2010

(65) Prior Publication Data
US 2011/0150790 A1    Jun. 23, 2011

(30) Foreign Application Priority Data
Aug. 29, 2008   (JP) ................................. 2008-222851

(51) Int. Cl.
| | | |
|---|---|---|
| *A61K 8/00* | (2006.01) | |
| *A61K 8/365* | (2006.01) | |
| *C07D 311/00* | (2006.01) | |
| *A61K 8/49* | (2006.01) | |
| *A23L 1/30* | (2006.01) | |
| *A61K 31/353* | (2006.01) | |
| *A61Q 11/00* | (2006.01) | |
| *C07D 311/62* | (2006.01) | |
| *A61K 9/00* | (2006.01) | |

(52) U.S. Cl.
CPC .............. *A61K 8/498* (2013.01); *A23L 1/3002* (2013.01); *A61K 31/353* (2013.01); *A61Q 11/00* (2013.01); *C07D 311/62* (2013.01); *A23V 2002/00* (2013.01); *A61K 9/0053* (2013.01); *A61K 9/0095* (2013.01); *A61K 2800/782* (2013.01)

(58) Field of Classification Search
USPC ........................................ 424/49, 55; 549/399
See application file for complete search history.

(56) References Cited

U.S. PATENT DOCUMENTS

| | | | |
|---|---|---|---|
| 5,409,692 A | 4/1995 | Nakahara et al. | |
| 5,629,338 A | 5/1997 | Okuda et al. | |
| 5,932,623 A | 8/1999 | Tanabe et al. | |
| 5,994,413 A | 11/1999 | Tanabe et al. | |
| 6,294,190 B1 | 9/2001 | Nakahara et al. | |
| 7,989,492 B2 * | 8/2011 | Nakai et al. ................... 514/456 |
| 2006/0079467 A1 | 4/2006 | Jia et al. | |
| 2008/0275258 A1 | 11/2008 | Nakai et al. | |

FOREIGN PATENT DOCUMENTS

| | | |
|---|---|---|
| EP | 0415126 A1 | 3/1991 |
| EP | 0853943 A1 | 7/1998 |
| EP | 1754702 A1 | 2/2007 |
| EP | 2193723 A1 | 6/2010 |
| JP | 58032875 A | 2/1983 |
| JP | 01102022 A | 4/1989 |
| JP | H03086814 A | 4/1991 |
| JP | 3-201947 | 9/1991 |
| JP | 03219872 A | 9/1991 |
| JP | 3228664 A | 10/1991 |
| JP | 03-284625 | 12/1991 |
| JP | 03-284671 | 12/1991 |
| JP | 06-247959 | 9/1994 |
| JP | 06-279302 | 10/1994 |
| JP | 07061927 A | 3/1995 |
| JP | 07-242556 | 9/1995 |
| JP | 07-285876 | 10/1995 |
| JP | 09040689 A | 2/1997 |
| JP | 09-191830 | 7/1997 |
| JP | 10175874 A | 6/1998 |
| JP | 2000226329 A | 8/2000 |
| JP | 2004-244385 | 9/2004 |
| JP | 2005-154432 | 6/2005 |
| JP | 2005-336117 | 12/2005 |
| JP | 2005336117 A * | 12/2005 |
| JP | 2007-176845 | 7/2007 |
| JP | 2009-001531 | 1/2009 |
| WO | WO 2005116005 A1 * | 12/2005 |

OTHER PUBLICATIONS

Tanaka et al, "A Novel Black Tea Pigment and Two New Oxidation Products of Epigallocatechin-3-O-Gallate," J. Agric. Food Chem., vol. 53, No. 19, pp. 7571-7578 (2005).*
Supplementary European Search Report issued Aug. 24, 2011 in EP Application No. 09809791.8.
F. Hashimoto et al., "Tannins and Related Compounds. XC.[1)] 8-C-Ascorbyl (−)-Epigallocatechin 3-O-Gallate and Novel Dimeric Flavan-3-ols, Oolonghomobisflavans A and B, from Oolong Tea. (3)", Chem.Pharm.Bull. vol. 37, No. 12, pp. 3255-3263, Dec. 1989.
S. Hamada et al., "Peroxidase-catalyzed generation of catechin oligomers that inhibit glucosyltransferase from *Streptoccus sobrinus*," FEMS Microbiology Letters 143 pp. 35-40, Jul. 1996.
S. Otake et al., "Anticaries effects of polyphenolic compounds from Japanese green tea," Caries Res. 25, pp. 438-443, (1991).

(Continued)

Primary Examiner — Dennis J Parad
(74) Attorney, Agent, or Firm — Drinker Biddle & Reath LLP (57) ABSTRACT

Provided is a highly palatable and safe glucosyltransferase inhibitor or anti-dental caries agent. A glucosyltransferase inhibitor or anti-dental caries agent having an epigallocatechin gallate polymer or a salt thereof. Particularly, the above agent containing an epigallocatechin gallate polymer, which is a compound in which chroman rings are bonded at position 6 and/or 8 via a methylene group.

6 Claims, 5 Drawing Sheets

(56) References Cited

OTHER PUBLICATIONS

K. Nakahara et al., "Inhibitory Effect of Oolong Tea Polyphenols on Glucosyltransferases of Mutans *Streptococci*", Applied and Environmental Microbiology, vol. 59, No. 4, pp. 968-973, Apr. 1993.

T. Ooshima and S. Hamada, "Anti-caries of Oolong Tea Polyphenols," The Nippon Dental review No. 622, pp. 179-189, Aug. 1994 (in Japanese).

M. Matsumoto et al., "Molecular analysis of the inhibitory effects of oolong tea polyphenols on glucan-binding domain of recombinant glucosyltransferases from *Streptococcus mutans* MT8148", FEMS Microbiology Letters, vol. 228, pp. 73-80, Sep. 2003.

International Search Report mailed Oct. 13, 2009 in PCT/JP2009/064335 filed Aug. 14, 2009.

Hashimoto et al., "Evaluation of the Anti-oxidative Effect (in vitro) of Tea Polyphenols," Biosci. Biotechnol. Biochem., 67 (2), pp. 396-401, 2003.

Moreno et al., "Inhibitory Effects of Grape Seed Extract on Lipases," Nutrition 19, pp. 876-879, 2003.

Yoshikawa et al., "*Salacia reticulata* and its Polyphenolic Constituents with Lipase Inhibitory and Lipolytic Activities Have Mild Anti-obesity Effects in Rats," J. Nutri 132:1819-1824 (2002).

Han et al., "Anti-obesity action of oolong tea," International Journal of Obesity (1999) 23, pp. 98-105.

Iwata et al., "Effects of Oolong Tea on Plasma Lipids and Lipoprotein Lipase Activity in Young Women," J. Jpn. Soc. Nutr. Food Sci. 44, (1991), pp. 251-259 (English Translation).

Chin et al., "Clinical Efficacy of Oolong Tea on Anti-Simple Obesity" J. Japanese Soc. Clin. Nutri. (20(1):89-90 (1998) (translation).

International Search Report mailed Aug. 16, 2005 in PCT/JP2005/009666 filed May 26, 2005.

Hatano et al., "Flavan Dimers with Lipase Inhibitory Activity from *Cassia Nomame*," Phytochemistry, vol. 46, No. 5, 1997, pp. 893-900.

Nakai et al., "Inhibitory Effects of Oolong Tea Polyphenols Pancreatic Lipase in Vitro," Agricultural and Food Chemistry, 2005, vol. 53, pp. 4593-4598.

European Search Report issued Dec. 4, 2008, in EP Appln. No. 05743859.0.

Hashimoto et al., "Evaluation of Tea Folyphenals as Anti-HIV Agents," Bioorganic & Medicinal Chemistry Letters, vol. 6, No. 6, 1996, pp. 695-700.

Teramoto, "Development of Black Oolong Tea as a Food for Specified Health Use", Japanese Journal of Nutritional Assessment, 2006, vol. 23, No. 4, pp. 323-325 (Excerpt English Translation).

\* cited by examiner

Inhibitory action of EGCG dimer and trimer compounds on GTFB
(Amount of sample: 0.1 mg/ml)

Significant difference between each sample and control at a concentration of 0.1 mg/ml
(*P<0.01, **P<0.001)

Figure 8

Inhibitory action of EGCG dimer and trimer compounds on GTFC
(Amount of sample: 0.1 mg/ml)

Significant difference between each sample and control at a concentration of 0.1 mg/ml
(*P<0.01, **P<0.001)

Figure 9

Inhibitory action of EGCG trimer and tetramer compounds on GTFB
(Amount of sample: 0.05 mg/ml)

Significant difference between each sample and control at a concentration of 0.05 mg/ml
(*P<0.01, **P<0.001)

Figure 10

Inhibitory action of EGCG trimer and tetramer compounds on GTFC
(Amount of sample: 0.05 mg/ml)

Significant difference between each sample and control at a concentration of 0.05 mg/ml
(*P<0.01, **P<0.001)

GLUCOSYLTRANSFERASE INHIBITOR CONTAINING EPIGALLOCATECHIN GALLATE POLYMER AS ACTIVE INGREDIENT

CROSS REFERENCE TO RELATED APPLICATIONS

This application is the National Stage of International Application No. PCT/JP2009/064335, filed Aug. 14, 2009, and claims benefit of Japanese Application No. 2008-222851, filed Aug. 29, 2008, which are herein incorporated by reference in their entirety.

TECHNICAL FIELD

The present invention relates to a glucosyltransferase inhibitor containing an epigallocatechin gallate polymer as an active ingredient, and a food and drink in which the inhibitor is added.

BACKGROUND ART

Although various hypotheses were proposed as to a cause of dental caries in the past, at present, dental caries is recognized as a bacterial infectious disease based on the chemo-microbial theory of Miller. According to the theory, dental caries developmental mechanism is as follows: glucosyltransferase (GTF), which is produced by oral *streptococcus*, particularly, *Streptococcus mutans* (hereinafter simply referred to as "*S. mutans*"), produces sticky and insoluble polysaccharide (glucan) from sucrose in the mouth as a substrate. Bacterial cells of *S. mutans* adhere onto a tooth surface with the aid of glucan thus produced to form plaque. In the plaque, various microorganisms including *S. mutans* live together and propagate. An organic acid is produced by metabolism of these microorganisms, acts to reduce the pH within the plaque and decalcifies tooth enamel surface. In this manner dental caries develops and progresses. Furthermore, plaque formation is said to be a cause of not only dental caries but also periodontal disease and bad breath.

As described above, since plaque formed by oral *streptococcus* primarily including *S. mutans* is a cause of dental caries, suppressing plaque formation can be eventually an effective means for preventing development of dental caries.

Recently, as a substance having anti-dental caries action, catechins contained in plants have attracted attention. Patent Literature 1 reports that a flavonoid polymer having a molecular weight of 800 to 5000 produced by treating a flavonoid (a catechin) with peroxidase has stronger glucosyltransferase inhibitory action compared to before the treatment.

Non Patent Literature 1 reports that a flavonoid polymer inhibits the activity of glucosyltransferase derived from *Streptococcus sobrinus* by 50% in an amount of 2.5 µg/mL.

Patent Literature 2 reports that a flavonoid polymer having a molecular weight of 1000 to 10000 and produced by condensing a reduced product of a flavanone/flavanol or a leucocyanidin with a catechin is found to have glucosyltransferase inhibitory activity.

However, these flavonoid polymers are a mixture of flavonoid trimer to pentamer or a mixture of a dimer and a trimer thereof. The compounds contained in the mixture have not yet been isolated. Therefore, the glucosyltransferase inhibitory activity of each of the compounds has not yet been elucidated.

Of the tea daily taken, a mixture of catechins derived from non-fermented tea, i.e., green tea, has been reported to have a glucosyltransferase inhibitory activity (Non Patent Literature 2). However, it has been also reported that a sufficient anti-dental caries action was not obtained in a test using rats.

It has been reported that semi-fermented tea, i.e., oolong tea and their purified products have glucosyltransferase inhibitory activity (Patent Literature 3, Non Patent Literature 3, Non Patent Literature 4 and Non Patent Literature 5). It is also known that glucosyltransferase inhibitory activity is enhanced by treating green tea, oolong tea and black tea with heat (Patent Literature 4) and that glucosyltransferase inhibitory activity is enhanced by treating a catechin with heat (Patent Literature 5).

However, in any case, it has not been elucidated as to which compound in the mixture derived from tea has the activity.

CITATION LIST

Patent Literature

PTL 1: Japanese Patent Laid-Open No. 6-247959
PTL 2: Japanese Patent Laid-Open No. 7-242556
PTL 3: Japanese Patent Laid-Open No. 6-279302
PTL 4: Japanese Patent Laid-Open No. 3-284625
PTL 5: Japanese Patent Laid-Open No. 3-284671

Non Patent Literature

NPL 1: FEMS Microbiology Letters 143 (1996) 35-40, Hamada S. et al.
NPL 2: Caries Res. 25 (1991) 438-443, Otake S. et al.
NPL 3: Applied and Environmental Microbiology, 59, No. 4 (1993) 968-973, Nakahara K. et al.
NPL 4: The Nippon Dental review No. 622 (August 1994) 179-189, Ooshima T. and Hamada S.
NPL 5: FEMS Microbiology Letters 228 (2003) 73-80, Matsumoto M. et al.

SUMMARY OF INVENTION

Technical Problem

As described above, there have been reports on plant extracts, etc. having glucosyltransferase inhibitory activity. However these only report that a mixture derived from a plant extract has the activity; but do not clearly report on a specific active ingredient (compound). Thus it has been desired to identify the active ingredient. Furthermore, in the case where an inhibitor derived from a low palatable plant is used as a food and drink, flavor and safety are presumably affected. Therefore, it has been desired to search an active ingredient derived from a high palatable plant.

Solution to Problem

The present inventors focused on a component contained in tea daily taken and intensively conducted studies in consideration of use as a food and drink. As a result, they found that an EGCG polymer obtained by polymerizing (−)-epigallocatechin-3-O-gallate (hereinafter, also referred to as EGCG), which is a catechin contained in oolong tea, etc., particularly an EGCG trimer, has strong glucosyltransferase inhibitory activity. Based on the finding, the present invention was attained.

More specifically, the present invention is as follows.
1. A glucosyltransferase inhibitor containing an epigallocatechin gallate trimer or a salt thereof as an active ingredient.

2. The glucosyltransferase inhibitor according to item 1 above, in which the epigallocatechin gallate trimer is a compound in which chroman rings are bonded at position 6 and/or 8 via a methylene group.

3. The glucosyltransferase inhibitor according to item 2 above, in which the epigallocatechin gallate trimer is a compound selected from the group consisting of a compound having the following Formula (I):

[Chem. 1]

Formula (I)

a compound having the following Formula (II):

[Chem. 2]

Formula (II)

and a compound having the following Formula (III):

[Chem. 3]

Formula (III)

wherein R is a galloyl group represented by the following Formula A:

Formula A:

[Chem. 4]

Formula A

4. A glucosyltransferase inhibitor containing, as an active ingredient, a compound represented by the following Formula (IV):

[Chem. 5]

Formula (IV)

5. An anti-dental caries agent containing an epigallocatechin gallate trimer or a salt thereof as an active ingredient.

6. The anti-dental caries agent according to item 5 above, in which the epigallocatechin gallate trimer is a compound in which chroman rings are bonded at position 6 and/or 8 via a methylene group.

7. The anti-dental caries agent according to item 6 above, in which the epigallocatechin gallate trimer is a compound selected from the group consisting of the compound having the above Formula (I), a compound having the above Formula (II) and compound having the above Formula (III) wherein R is a galloyl group represented by the above Formula (A).

8. An anti-dental caries agent containing a compound represented by the above Formula (IV) as an active ingredient, 9. A food or drink, in which the glucosyltransferase inhibitor or the anti-dental caries agent according to any one of items 1 to 8 above is added.

10. The food or drink according to item 9 above, in which the food or drink is a tea beverage.

11. An organ hygiene product, in which the glucosyltransferase inhibitor or anti-dental caries agent according to any one of items 1 to 8 above is added.

Advantageous Effects of Invention

The present inventors found that a (−)-epigallocatechin-3-O-gallate (EGCG) polymer, particularly a predetermined EGCG dimer and trimer have high glucosyltransferase inhibitory action. As described above, since glucosyltransferase (hereinafter, also referred to as GTF) produces glucan (a cause of plaque) in a mouth, dental caries can be prevented by inhibiting the activity of GTF. Therefore, the GTF inhibitor of the present invention can be used as an anti-dental caries agent. Furthermore, since the GTF inhibitor of the present invention suppresses generation of glucan (a cause of plaque), the effect of suppressing bad breath is also expected. In addition, since the GTF inhibitor of the present invention is derived from EGCG contained in a food and drink daily taken such as oolong tea, it has a high palatability and high safety to a human body. Furthermore, by adding a predetermined amount of GTF inhibitor to a food and drink, a food and drink having a high palatability, safety and an anti-dental caries action can be provided without excessively damaging flavor.

DESCRIPTION OF EMBODIMENTS

Epigallocatechin Gallate Polymer (−)-Epigallocatechin-3-O-gallate (EGCG) is a major component of a catechin contained in green tea, etc. and a compound having a structure represented by the following Formula:

[Chem. 6]

An active ingredient contained in the GTF inhibitor of the present invention is the EGCG polymer mentioned above. in the present invention, in particular, an EGCG polymer having EGCG in which 2 or 3 chroman rings are bonded at position 6 and/or 8 via a methylene group, can be preferably used. Specific examples of such EGCG polymer include EGCG trimers represented by the following Formula (I), Formula (II) and Formula (III):

[Chem. 7]

Formula (I)

[Chem. 8]

Formula (II)

[Chem. 9]

Formula (III)

wherein R is a galloyl group, and EGCG dimer represented by the following Formula (IV):

[Chem. 10]

Formula (IV)

The compound of Formula (I) can be expressed as EGCG8:8 EGCG6:8 EGCG based on the coupling scheme of EGCG (hereinafter, in the specification, referred to as oolong homobisflavan-trimer-1, OHBF-Tri-1 or Tri-1). Similarly, the compound of Formula (II) can be expressed as EGCG6:8 EGCG6:8 EGCG (hereinafter, in the specification, referred to as oolong homobisflavan-trimer-2, OHBF-Tri-2 or Tri-2). Furthermore, the compound of Formula (III) can be expressed as EGCG8:8 EGCG6:6 EGCG (hereinafter, in the specification, referred to as oolong homobisflavan-trimer-4, OHBF-Tri-4 or Tri-4). The compound of Formula (IV) can be expressed as EGCG6:8 EGCG. The compound of Formula (IV) is reported as a compound contained in oolong tea, etc. and known as oolong homobisflavan-B (OHBF-B). Note that the compounds of Formulas (II) and (III) are novel compounds.

The EGCG polymers mentioned above can be each produced by reacting epigallocatechin gallate with formaldehyde in a solvent in the presence of an acid.

Examples of the solvent that can be used in the reaction include alcohols such as methanol, ethanol, n-propanol and isopropanol. The amount of solvent used is not particularly limited; however, for example, 20 to 200 parts by mass of solvent can be used relative to 1 part by mass of epigallocatechin gallate.

Examples of the acid that can be used include inorganic acids such as hydrochloric acid, sulfuric acid and nitric acid and organic acids such as formic acid and acetic acid. The amount of acid used is not particularly limited; however, 0.01 to 2 moles of acid can be used relative to 1 mole of epigallocatechin gallate.

The amount of formaldehyde that can be used is, for example, 1 to 100 moles relative to 1 mole of EGCG.

Reaction temperature and time may vary depending upon e.g., the amount of solvent to be used; however, for example, reaction temperature is −10 to 50° C., and reaction time is 10 minutes to 12 hours. Typically, the reaction temperature is room temperature (about 25° C.).

The product obtained by the reaction of EGCG with formaldehyde is generally a mixture containing at least two compounds different in coupling scheme of chroman rings by a methylene group. From such a mixture, compounds of Formulas (I) to (IV) can be isolated by using a known purification method such as open column chromatography using a styrene based adsorption resin such as HP-20 (manufactured by Mitsubishi Chemical Corporation) and a dextran based resin such as Shephadex LH-20 and high performance liquid chromatography (HPLC).

Note that a preparation method for the compound of Formula (I) (OHBF-Tri-1) is described as a synthesis and purification method for "trimer (4)" in Patent Literature (WO2005/116005). Furthermore, a preparation method of the compound of Formula (IV) (OHBF-B) is described in the literature (Chem. Pharm. Bull 37 (12), 3255-3563 (1989)).

The EGCG polymer that can be used as a glucosyltransferase inhibitor of the present invention may be in the form of a salt. Such a salt is not particularly limited as long as it is a pharmaceutically acceptable salt or an acceptable salt as a food. Examples thereof include a salt with a metal element belonging to the first or second family of the periodic table, such as a lithium salt, a sodium salt, a potassium salt, a calcium salt and a magnesium salt. Such a metal salt can be formed with, for example, a phenolic hydroxide group of EGCG.

For example, a sodium salt of an EGCG trimer can be produced by reacting the EGCG trimer and metallic sodium or sodium hydride in a non-protic solvent to convert a hydroxide group (—OH) contained in the EGCG trimer to a sodium alkoxide group (—ONa). At this time, all hydroxide groups contained in the EGCG trimer can be converted into sodium alkoxide groups and only part of the hydroxide groups can be converted into sodium alkoxide groups by controlling the amount of metallic sodium or sodium hydride used.

These EGCG polymers can be synthetically obtained; however, as described in Example 5 later, they were found to be present also in oolong tea. Therefore, the active ingredient of the GTF inhibitor of the present invention, i.e., EGCG polymer, can be isolated from tea leaves using the leaves of *Camellia sinensis* [A1] as a raw material, preferably from fermented tea such as oolong tea and black tea and roasted tea by extraction and purification.

<GTF Inhibitor or Anti-Dental Caries Agent Containing EGCG Polymer as Active Ingredient>

The present inventors found that an EGCG polymer, particularly the compound of the above Formula (I), i.e., oolong homobisflavan-trimer-1, the compound of Formula (II) i.e., oolong homobisflavan-trimer-2, the compound of Formula (III) i.e., oolong homobisflavan-trimer-4, and the compound of Formula (IV) i.e., oolong homobisflavan-B have high glucosyltransferase inhibitory activity.

The glucosyltransferase inhibitory activity can be measured by using any one of the evaluation methods described in prior-art literatures set forth in Background Art. For example, glucosyltransferase prepared from *Streptococcus mutans* etc. is added to an aqueous solution containing sucrose, and incubated at about the same temperature (about 37° C.) as in the oral cavity for less than 24 hours, preferably about 16 to 20 hours to enzymatically produce glucan from sucrose. Since glucan is insoluble in water, the turbidity of the resultant reaction solution (for example, turbidity at a wavelength of 550 nm) is measured. In this manner, the yield of glucan can be evaluated. If the yield of glucan low (in other words, turbidity is low), it is said that glucosyltransferase activity is more inhibited than that of the case where the yield of glucan is large (in other words, turbidity is high).

Since the glucosyltransferase inhibitor of the present invention inhibits the activity of glucosyltransferase (GTF) to thereby suppress production of glucan (a cause of plaque formation in a mouth), it can be used as an anti-dental caries agent.

Since the glucosyltransferase inhibitor or anti-dental caries agent of the present invention is derived from EGCG contained in a food and drink, such as oolong tea, daily taken, it is highly palatable and highly safe to a human body.

<Food and Drink>

The glucosyltransferase inhibitor or anti-dental caries agent of the present invention can be added to various types of foods and drinks for preventing dental caries such as tooth decay. Examples of foods and drinks to which the glucosyltransferase inhibitor or anti-dental caries agent of the present invention is to be added include beverages such as refreshing drinks, tea drinks, liquid tonic medicines, healthy drinks, nutrition drinks, sports drinks and carbonated drinks (including concentrated stock solutions and preparatory powders of these beverages) and foods such as gums, candies, jellies, tablets, health foods, nutrition foods and supplements.

The addition amount to a food and drink is not particularly limited as long as a desired effect can be obtained, and can be appropriately determined in view of e.g., taste, color and flavor of a food and drink. For example, when a beverage for anti-dental caries is prepared, an EGCG polymer can be added to the beverage in a concentration of about 0.01 to 1000 ppm. Furthermore, when an EGCG polymer is added to a solid food, the EGCG polymer can be added in about 0.01 to 5000 μg/g based on the weight of the solid food.

<Oral Hygiene Product>

Since the glucosyltransferase inhibitor or anti-dental caries agent of the present invention inhibits the activity of glucosyltransferase (GTF), thereby suppressing generation of glucan, (a cause of plaque formation), it can be used as an oral hygiene product, for example, for preventing tooth decay and bad breath. Examples of the oral hygiene product according to the present invention include a toothpaste, a mouthwash and a troche. These oral hygiene products can be produced using a carrier conventionally used in the art by a conventional process. Examples of the carrier that can be used include various types of organic or inorganic carrier substances conventionally used as a preparation material. Furthermore, if necessary, additives for a preparation such as a preservative, an antioxidative agent, a coloring agent and a sweetening agent can be blended. The addition amount of GTF inhibitor or anti-dental caries agent of the present invention to an oral hygiene product can be appropriately determined depending upon e.g., the form of an oral hygiene product; for example, an EGCG polymer can be added to an oral hygiene product so as to obtain a concentration of about 0.0001 to 10 wt %.

The present invention will be described in more detail by way of Examples; however, the present invention is not limited by these.

Example 1

Synthesis and Purification of EGCG Polymer

A. Synthesis and Fractionation by Open Column:

Six gram of (−)-epigallocatechin-3-O-gallate (EGCG) (Teavigo (registered trade mark) manufactured by Roche) was dissolved in 120 ml of ethanol containing 0.02N HCl, and a 4% formaldehyde ethanol solution (180 ml) was added and then stirred at room temperature for 4 hours. After completion of the reaction, the resultant reaction solution was diluted 10 fold with pure water and applied on an adsorption resin CHP-20P column (600 ml, 37-75 mm, manufactured by Mitsubishi Chemical Corporation). After washed with water (1200 ml), elution was performed sequentially with 900 ml of 25% $CH_3CN$ and 1200 ml of 30% $CH_3CN$. The elution fraction with 25% $CH_3CN$ was separated into three fractions (fr. 1 to fr. 3) of 300 ml for each, whereas the elution fraction with 30% $CH_3CN$ was separated into four fractions (fr. 4 to fr. 7) of 300 ml for each.

B. Preparative HPLC Conditions:

The fractionated products obtained by the CHP-20P column purification was further purified by reverse-phase preparative HPLC.

<Conditions>

Column: Develosil ODS-HG-5 (5 cm φ×50 cm, manufactured by Nomura Chemical Co., Ltd.)

Mobile phase: A: 0.05% TFA/H2O, B: 90% CH3CN/0.05% TFA/H2O,

Flow rate: 32 ml/min

Gradient program: isocratic at A80%/B20% (30 min), gradient from A80%/B20% to A60%/B40% (100 min), isocratic at A60%/B40% (20 min)

Detection: A 280 nm

Sample: fr. 2 to fr. 7 obtained by CHP-20P column purification each were dissolved in 20% $CH_3CN$ and the total amount was applied by several times.

In the above fractionation conditions, individual peaks corresponding to retention time 113 minutes (compound 1), 120 minutes (compound 2), 130 minutes (compound 3) and retention time 85 minutes (compound 4), retention time 106 minutes (compound 5) and retention time 104 minutes (compound 6) were collected.

C. Structural Analysis of Compound:

The compounds isolated by preparative HPLC were subjected to MS and NMR measurements. Of them, MS of compounds 4 to 6 were measured by Q-TOF Premier (manufactured by Micromass, UK) in a negative, V mode. As a result, ion peaks thereof were observed respectively at m/z 927.160, 927.163, and 1397.248 [M-H]−. Furthermore, NMR spectrum data of compound 4 coincided with the NMR spectrum data of oolong homobisflavan-A described in the literature (Chem. Pharm. Bull 37(12), 3255-3563 (1989)). The NMR spectrum data of compound 5 coincided with the NMR spectrum data of oolong homobisflavan-B described in the literature (Chem. Pharm. Bull 37(12), 3255-3563 (1989)). Furthermore, from the NMR spectrum data of compound 6, compound 6 was identified as the compound of Formula (I), namely, oolong homobisflavan-trimer-1. From these results, it was confirmed that compound 4 is an EGCG dimer having a coupling scheme of EGCG8:8 EGCG, i.e., oolong homobisflavan-A (OHBF-A); compound 5 is an EGCG dimer having a coupling scheme of EGCG6:8 EGCG, i.e., oolong homobisflavan-B (OHBF-B); and compound 6 is a EGCG trimer having a coupling scheme of EGCG8:8 EGCG6:8 EGCG, i.e., oolong homobisflavan-trimer-1 (in this application, also referred to as OHBF-Tri-1 or Tri-1). Note that the bond between EGCG moieties expressed as 6:8 or 8:8 represents the state where carbon at position 6 or 8 of A ring of EGCG is crosslinked with a counterpart via a methylene group sandwiched between them. The structural formulas of individual compounds are shown below.

[Chem. 11]

OHBF-A

[Chem. 12]

OHBF-B

[Chem. 13]

-continued

Tri-1

With respect to compound 1 to compound 3, structural analysis was performed by MS and NMR. MS was measured by Q-TOF Premier (manufactured by Micromass, UK) using ESI equipped with a Z spray ion source as an ion source in a negative, V mode. Mass correction was performed by lock spray at a Cone voltage: 45V, Capillary voltage: 3 KV, Source Temp: 80° C., and Desolvation Temp: 180° C. As a reference, leucine enkephalin (m/z 554.2615 [M-H]$^-$) was used.

As a result, compound 2 gave molecular ions of m/z 1397.2479 [M-H]$^-$ and a molecular formula thereof was calculated as $C_{68}H_{54}O_{33}$ (err.: 0.7 ppm); and compound 3 gave molecular ions of m/z 1397.2509 [M-H]$^-$ and a molecular formula thereof was calculated as $C_{68}H_{54}O_{33}$ (err.: 2.9 ppm). They were estimated as substances having three EGCG molecules crosslinked with two methylene groups. Furthermore, compound 1 gave molecular ions of m/z 1867.3100 [M-H]$^-$ and divalent 933.1151 [M-2H]$^{2-}$ and a molecular formula thereof was calculated as $C_{91}H_{72}O_{44}$ (err.: -11.7 ppm) and estimated as a substance having four EGCG molecules crosslinked with three methylene groups.

NMR was measured by dissolving compound 2 in $CD_3OH$ and compound 3 in DMSO-d6 (($CD_3$)$_2$SO). Residual peaks of a proton of $CD_3OH$ and $^{13}C$, i.e., δ 3.30 and δ 48.97 were used as the internal standards of compound 2. Residual peak of $^1H$ of DMSO-d6, i.e., δ 2.50 and that of $^{13}C$, i.e., δ 39.43 were used as the internal standards of compound 3. Measurement items, which were $^1H$ NMR, $^{13}C$ NMR, $^1H\{^{13}C\}$-HSQC, $^1H\{^{13}C\}$-HMBC, TOCSY and DQF-COSY, were measured by DMX-750 spectrometer (BRUKER BIOSPIN, Germany). As a result of the NMR, it was elucidated that compound 2 is the compound of Formula (II) above (more specifically, oolong homobisflavan-trimer-2 and also referred herein to as OHBF-Tri-2 or Tri-2) having a coupling scheme of EGCG6:8 EGCG6:8 EGCG; and that compound 3 is the compound of Formula (III) above (more specifically, oolong homobisflavan-trimer-4 and also referred herein to as OHBF-Tri-4 or Tri-4) having a coupling scheme of EGCG8:8 EGCG6:6 EGCG. The $^1H$ NMR and $^{13}C$ NMR spectra of compounds 2 and 3 are shown in FIGS. 1 to 4.

Compound 2:

With respect to oolong homobisflavan-trimer-2 (in $CD_3OH$), signals of $^1H$ NMR observed were δ 6.95, 6.92, 6.90, 6.60, 6.54, 6.44, 6.08, 6.02, 5.57, 5.55, 5.49, 5.18, 5.12, 4.91, 3.86, 3.83, 3.81, 3.76, 3.03, 3.01, 2.94, 2.89, 2.89, 2.82 and signals of $^{13}C$ NMR observed were δ 167.72, 167.46, 167.37, 156.29, 155.25, 155.08, 154.79, 154.43, 153.64, 152.91, 151.64, 151.20, 147.00, 146.93, 146.38, 146.38, 146.34, 146.29, 140.03, 139.89, 139.89, 134.65, 134.48, 133.85, 130.64, 129.29, 129.10, 121.33, 121.14, 121.14, 110.31, 110.24, 110.24, 109.19, 108.07, 107.42, 107.05, 107.02, 106.79, 106.10, 101.59, 101.00, 100.45, 97.23, 96.71, 80.07, 79.94, 78.45, 70.00, 69.32, 69.28, 27.21, 27.21, 26.81, 17.91, 17.91.

Compound 3:

With respect to oolong homobisflavan-trimer-4 (in DMSO-d6) signals of $^1H$ NMR observed were δ 10.46, 9.18, 9.16, 9.16, 9.12, 9.06, 9.05, 8.90, 8.88, 8.84, 8.72, 8.69, 8.69, 8.46, 8.34, 8.05, 8.02, 8.00, 6.81, 6.78, 6.78, 6.52, 6.47, 6.35, 6.03, 5.93, 5.48, 5.46, 5.39, 5.04, 4.95, 4.89, 4.05, 3.95, 3.56, 3.56, 3.06, 3.00, 2.98, 2.76, 2.71, 2.67 and signals of $^{13}C$ NMR observed were δ 165.11, 165.09, 164.99, 157.66, 154.29, 153.82, 153.48, 153.07, 152.68, 152.23, 152.18, 150.88, 145.56, 145.52, 145.50, 145.26, 145.24, 145.23, 138.43, 138.43, 138.39, 132.34, 132.23, 132.19, 128.34, 128.34, 128.23, 119.17, 119.12, 119.04, 110.35, 110.31, 110.29, 109.19, 108.59, 108.56, 108.51, 106.97, 106.63, 105.26, 105.26, 105.13, 104.73, 101.28, 99.44, 99.41, 98.21, 97.34, 97.15, 96.03, 79.48, 79.07, 78.47, 69.95, 69.39, 69.28, 27.18, 26.98, 26.58, 18.16, 17.13.

Figure 1:
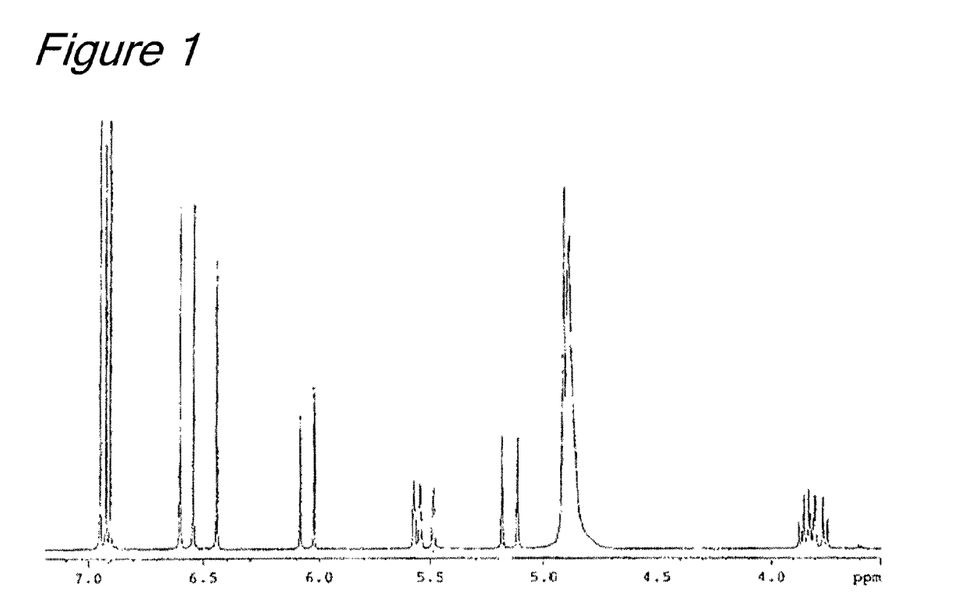
FIG. 1 shows a $^1$H NMR spectrum of compound 2.
Figure 2:
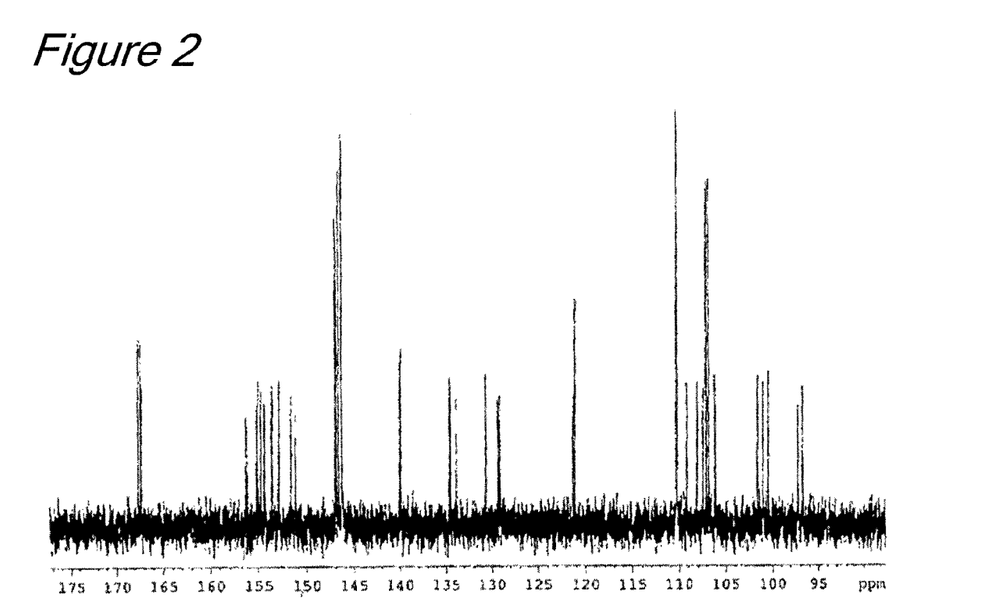
FIG. 2 shows a $^{13}$C NMR spectrum of compound 2.
Figure 3:
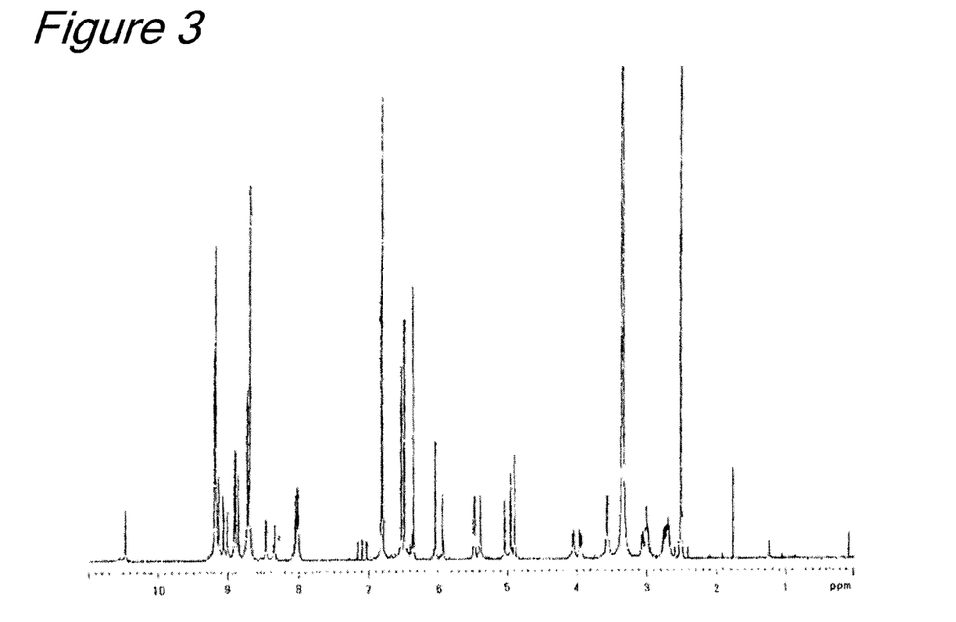
FIG. 3 shows a $^1$H NMR spectrum of compound 3.
Figure 4:
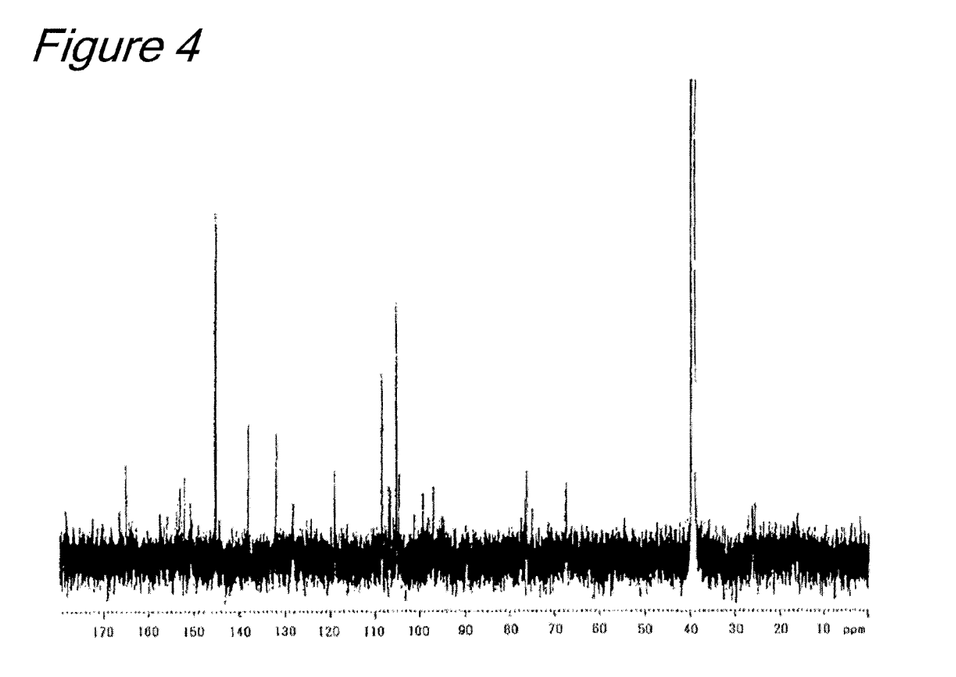
FIG. 4 shows a $^{13}$C NMR spectrum of compound 3.
Figure 5:
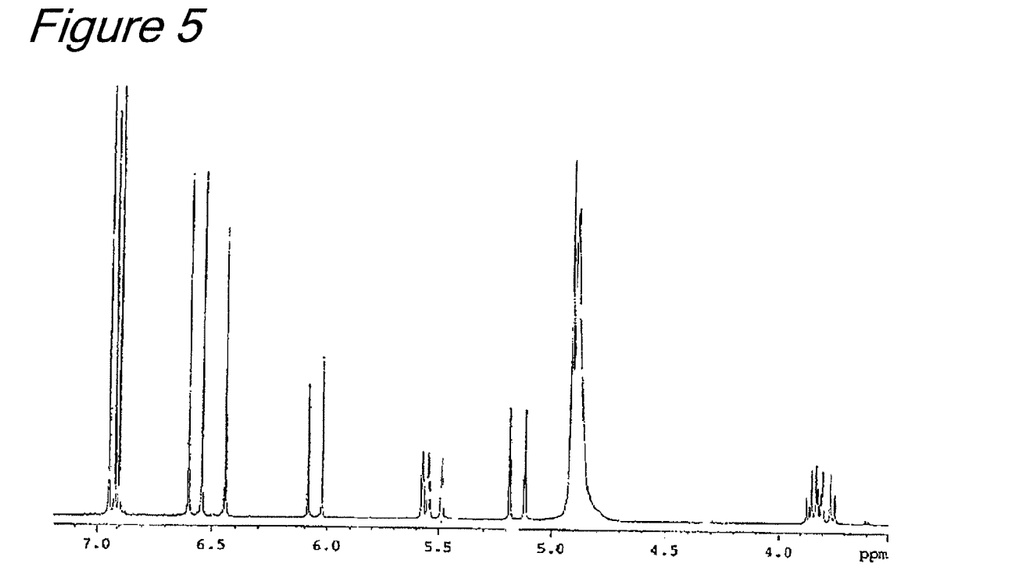
FIG. 5 shows a $^1$H NMR spectrum of compound 1.
Figure 6:
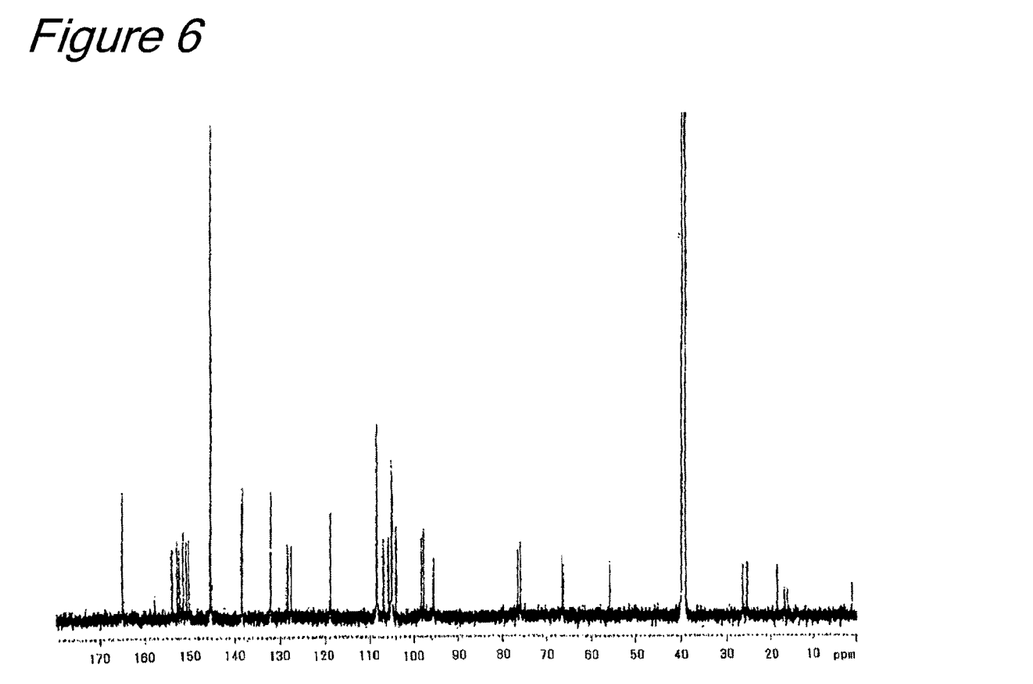
FIG. 6 shows a $^{13}$C NMR spectrum of compound 1.

Furthermore, compound 1 was dissolved in DMSO-d6 and subjected to NMR measurement using residual peaks of $^1H$ and $^{13}C$, i.e., δ 2.50 and δ 39.43, as the internal standards. Measurement items, which were $^1H$ NMR, $^{13}C$ NMR, $^1H\{^{13}C\}$-HSQC, $^1H\{^{13}C\}$-HMBC, TOCSY and DQF-COSY, were measured by DMX-750 spectrometer (BRUKER BIOSPIN, Germany). As a result of NMR, it was elucidated that compound 1 is an EGCG tetramer having a coupling scheme of EGCG8:6 EGCG8:8 EGCG6:8 EGCG (oolong homobisflavan-tetramer-2, and also referred herein to as OHBF-Tet-2 or Tet-2). The $^1H$ NMR and $^{13}C$ NMR spectra of compound 1 are shown in FIG. 5 and FIG. 6.

Compound 1:

With respect to oolong homobisflavan-tetramer-2, signals of $^1H$ NMR (in DMSO-d6) observed were δ 9.91, 9.25, 9.16, 8.09, 7.22, 6.81, 6.76, 6.74, 6.52, 5.94, 5.50, 5.38, 4.77, 4.52, 3.95, 3.95, 3.80, 3.54, 2.80, 2.74, 2.73, 2.67 and signals of $^{13}C$ NMR observed were δ 165.08, 165.01, 154.06, 152.83, 152.35, 151.45, 150.78, 150.26, 145.52, 145.52, 145.24, 145.18, 138.49, 138.44, 132.21, 132.10, 128.42, 127.63, 119.05, 118.95, 108.58, 108.46, 108.46, 106.95, 105.74, 104.92, 104.06, 98.32, 97.81, 76.59, 75.94, 66.69, 66.35, 26.33, 25.26, 16.72, 15.99.

The structural formulas of the individual compounds identified as mentioned above are shown below.

[Chem. 14]

Tri-2

[Chem. 15]

Tri-4

[Chem. 16]
-continued

Tet-2

The yields of the individual compounds obtained by the aforementioned synthesis and purification procedure were as follows:
oolong homobisflavan-A (984 mg), oolong homobisflavan-B (374 mg), oolong homobisflavan-trimer-1 (468 mg), oolong homobisflavan-trimer-2 (73 mg), oolong homobisflavan-trimer-4 (12 mg) and oolong homobisflavan-tetramer-2 (44 mg).

Example 2

Preparation of Recombinant Glucosyltransferase (rGTF)

rGTF was prepared by the method described in the paper of M. matsumoto et al, FEMS Microbiology Letters 228 (2003) 73-80. More specifically, *Escherichia coli* XL-2 strain harboring a plasmid pSK6 having a gene encoding glucosyltransferase B (GTFB) of *Streptococcus mutans* was subjected to shaking culture performed in Luria Bertani liquid medium containing ampicillin (100 μg/mL) and tetracycline (7.5 μg/mL) at 37° C. for 16 hours. Bacterial cells were collected by centrifugally separating the medium, suspended in a 10 mM phosphate buffer (pH 6.5) previously cooled and crushed by an ultrasonic generator (UD201 type, manufactured by Tomy Seiko Co., Ltd., Tokyo) under ice cooling. After crushed, precipitates were centrifugally removed at 12,000×g for 30 minutes. The resultant supernatant was used as glucosyltransferase B (rGTFB) and put in use in later experiments.

Similarly, recombinant glucosyltransferase C (rGTFC) was prepared by using *Escherichia coli* XL-2 strain harboring a plasmid pSK6 having a gene encoding glucosyltransferase C (GTFC) of *Streptococcus mutans* and put in use in later experiments.

The rGTFB having a specific activity of 503 mU/mg protein and the rGTFC having a specific activity of 6.3 to 22.3 mU/mg protein were used as a mixture. The activity 1U represents activity of an enzyme in converting glucose (1.0 mM) derived from sucrose into glucan per minute. Protein was quantified by using the bicinchonine acid method (BCA method) (BCA protein assay kit, manufactured by PIERCE).

Example 3

Evaluation of Glucosyltransferase Inhibitory Activity
(1)

Oolong homobisflavan-A (OHBF-A), oolong homobisflavan B (OHBF-B) and oolong homobisflavan-trimer-1 (Tri-1) obtained in Example 1 and theasinensin A (TSN-A) prepared in accordance with the paper (Hashimoto, F. Nonaka, G. Nishioka, I. Chem. Pharm. Bull. 36 (5), 1676-1684 (1988)) were each evaluated for a glucosyltransferase (GTF) inhibitory activity by the following procedure. Note that theasinensin A (TSN-A) used herein as a reference is a substance in which B rings of EGCG are mutually bonded symmetrically at the 2' positions and having the following structure:

[Chem. 17]

TSN-A

Figure 7:
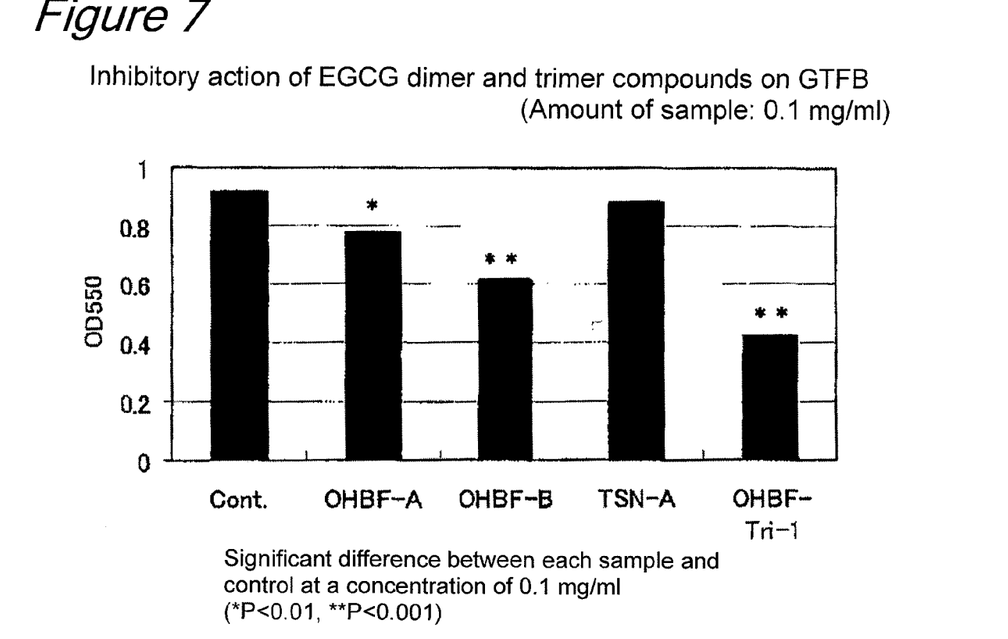
FIG. 7 shows the evaluation results of the inhibitory action of each of EGCG dimer and trimer compounds on glucosyltransferase B.
Figure 8:
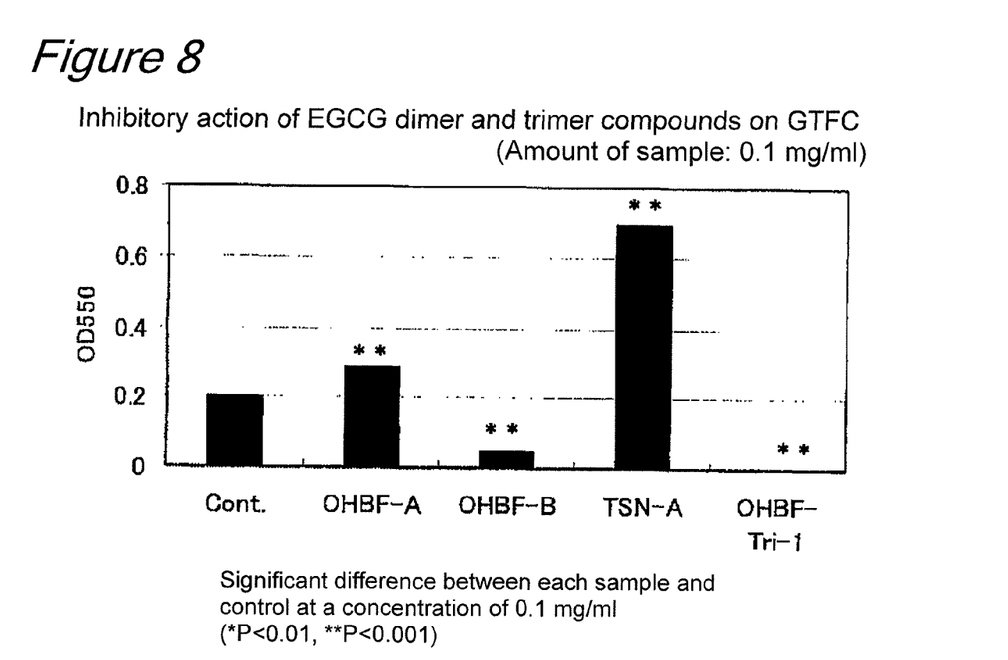
FIG. 8 shows the evaluation results of the inhibitory action of each of EGCG dimer and trimer compounds on glucosyltransferase C.

With 2 mL of 0.1M KPB (pH6.0) containing 1% sucrose-containing 0.1% dextran T10, rGTFB or rGTFC (amount corresponding to 15 mU (average value)) obtained in Example 2, and each of the above samples (final concentration: 0.1 mg/mL) were mixed. The mixture was incubated at 37° C. overnight. The turbidity (550 nm) of the resultant reaction solution was measured to obtain the yield of glucan insoluble in water. The lower yield of the glucan insoluble in water (in other words, turbidity is low) means that the activity of glucosyltransferase is more inhibited. The results are shown in FIG. 7 and FIG. 8. Note that the control (cont) shown in the figures represents turbidity in the absence of the aforementioned samples.

As shown on FIGS. 7 and 8, it was found that OHBF-A inhibits the activity of GTFB and slightly enhances the activity of GTFC, conversely. Furthermore, it was found that TSN-A has substantially no effect upon the activity of GTFB and extremely enhances the activity of GTFC, conversely. On the other hand, it was found that OHBF-B and OHBF-Tri-1 inhibit the activities of both GTFB and GTFC. Particularly, a trimer, OHBF-Tri-1, most strongly inhibits the activities of both GTFB and GTFC compared to other dimer compounds.

Example 4

Evaluation of Glucosyltransferase Inhibitory Activity
(2)

Oolong homobisflavan-trimer-1 (OHBF-Tri-1), oolong homobisflavan-trimer-2 (OHBF-Tri-2), oolong homobisflavan-trimer-4 (OHBF-Tri-4) and oolong homobisflavan-tetramer-2 (OHBF-Tet-2) obtained in Example 1 were each evaluated for a glucosyltransferase (GTF) inhibitory activity by the following procedure.

Figure 9:
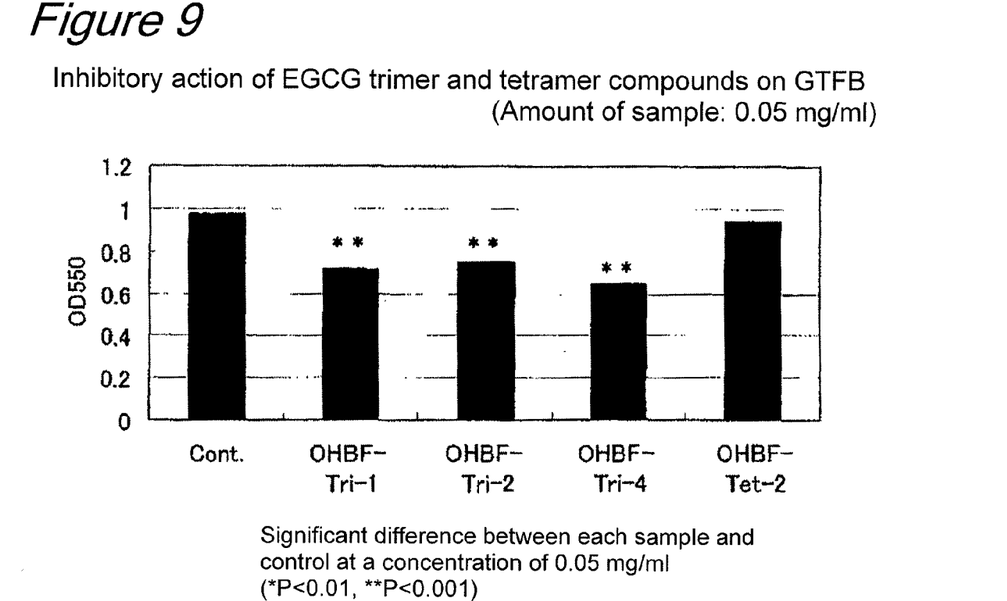
FIG. 9 shows the evaluation results of the inhibitory action of each of EGCG trimer and tetramer compounds on glucosyltransferase B.
Figure 10:
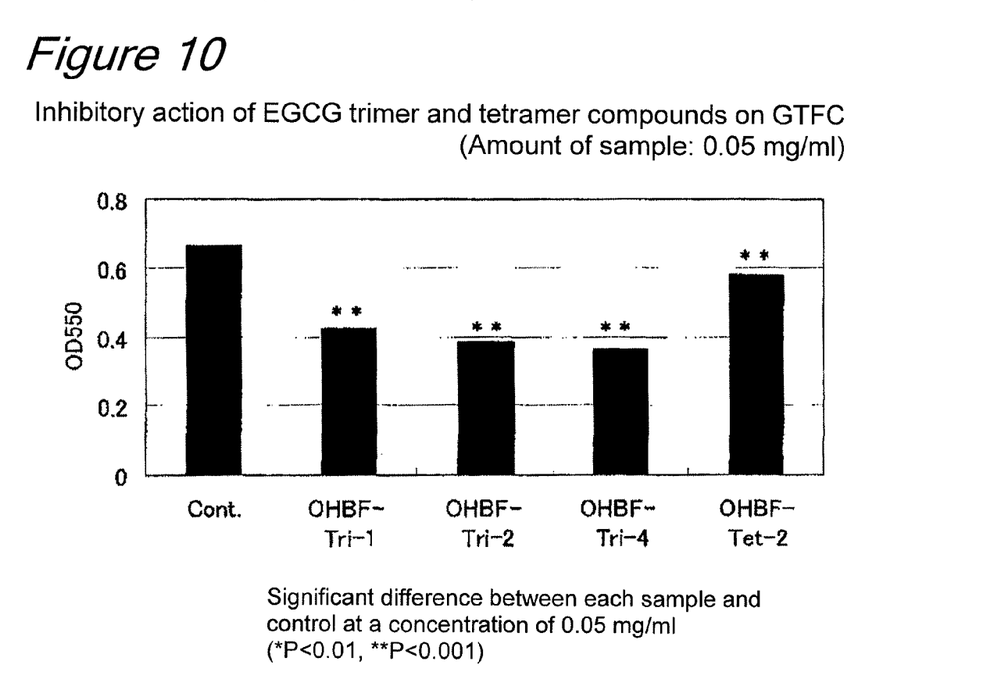
FIG. 10 shows the evaluation results of the inhibitory action of each of EGCG trimer and tetramer compounds on glucosyltransferase C.

With 2 mL of 0.1M KPB (pH6.0) containing 1% sucrose and 0.1% dextran T10, rGTFB or rGTFC (amount corresponding to 15 mU (average value)) obtained in Example 2 and each of the above samples (final concentration: 0.05 mg/mL) were mixed. The mixture was incubated at 37° C. overnight. The turbidity (550 nm) of the resultant reaction solution was measured to obtain the yield of glucan insoluble in water. The lower yield of the glucan insoluble in water (in other words, turbidity is low) means that the activity of glucosyltransferase is more inhibited. The results are shown in FIG. 9 and FIG. 10. Note that the control (cont) shown in the figures represents turbidity in the absence of the aforementioned samples.

As shown on FIGS. 9 and 10, an EGCG tetramer, i.e., Tet-2, slightly inhibited the activity of GTFC; however a significant inhibitory effect on GTFB was not confirmed. On the other hand, it was confirmed that EGCG trimers, Tri-1, Tri-2, and Tri-4, each have inhibitory activities on GTFB and GTFC. The inhibitory action on GTFB was higher than an EGCG tetramer, Tet-2.

From the aforementioned results, it was found that EGCG trimers, i.e., Tri-1, Tri-2, and Tri-4, and an EGCG dimer, i.e., OHBF-B have high GTF inhibitory activity. Particularly, it was found that EGCG trimers, i.e., Tri-1, Tri-2 and Tri-4, have a higher GTF inhibitory activity than EGCG dimers, i.e., OHBF-A, OHBF-B and TSN-A, and an EGCG tetramer, i.e., Tet-2.

Example 5

Quantification of Polymerized Polyphenol by LC-MS/MS Measurement Conditions of Trimer and Tetramer by LC-MS/MS and Quantification of "Suntory Black Oolong Tea" (Manufactured by Suntory Limited.)

LC-MS/MS of an EGCG polymer was measured by 4000 Q TRAP (manufactured by Applied) using turbo ion spray in the following conditions: Collision energy: 46 eV (nega.), Ion spray voltage: 4500V, Temp: 450° C.

As a measurement channel for each compound in MRM (multiple reaction monitoring), 698.40/168.90 (nega. divalent) was used for oolong homobisflavan-trimers, and oolong homobisflavan-trimer-1 was used as a standard substance. A channel of 933.16/168.90 (nega. divalent) was used for oolong homobisflavan-tetramers and oolong homobisflavan-tetramer-2 was used as a standard substance. Measurement was carried out in the following conditions.

Column: Develosil C30-UG-3 (manufactured by Nomura Chemical Co., Ltd., 3 mmϕ×150 mm)
Flow rate: 0.3 ml/min,
Column Temp.: 40° C.
Mobile phase A: 0.1% HCOOH/$H_2O$,
Mobile phase B: 0.1% HCOOH/$CH_3CN$
Gradient program: A91%/B9% (0 min)→A40%/B60% (17 min)→A15%/B85% (17.1 min), subsequently isocratic (17.1 to 19 min) at A15%/B85%

Since these compounds were contained only in a trace amount in "Suntory Black oolong tea", it was impossible to directly quantify them. Then, "Suntory Black oolong tea" (before sterilized) was fractionated stepwise by a CHP-20P column (manufactured by Mitsubishi Chemical Corporation). After each of the fractions was quantified, the concentrations of individual fractions detected were added up to obtain the concentration in the original tea. The concentration in "Suntory Black oolong tea" was obtained as follows. The concentration of trimers was obtained by converting the concentrations of five components detected in terms of oolong homobisflavan-trimer-1 and adding them up. It was 172 ng/ml. The concentration of tetramers was obtained by adding up the concentrations of four components detected. It was 55 ng/ml in terms of oolong homobisflavan-tetramer-2.

The invention claimed is:

1. A method for inhibiting glucosyltransferase activity in a subject comprising:
    preparing an isolated epigallocatechin gallate (EGCG) trimer or a salt thereof from black tea or roasted tea:
    preparing a composition comprising the isolated EGCG trimer or a salt thereof; and
    administering the composition to a subject in need thereof;
    wherein the EGCG trimer or a salt thereof is selected from the group consisting of a compound having the following Formula (II):

[Formula II]

and a compound having the following formula (III):

[Formula III]

or a mixture thereof;
wherein R is a galloyl group represented by the following Formula A:

[Formula A]

(A)

2. The method according to claim 1 wherein the composition is a food or drink.
3. The method according to claim 2 wherein the food or drink is a tea beverage.
4. A method for hindering dental caries and/or bad breath in a subject comprising:
    preparing an isolated epigallocatechin gallate (EGCG) trimer or a salt thereof from black tea or roasted tea;

preparing a composition containing the isolated EGCG trimer or a salt thereof; and administering the composition to a subject in need thereof;

wherein the EGCG trimer or a salt thereof is selected from the group consisting of a compound having the following Formula (II):

[Formula II]

and a compound having the following formula (III):

[Formula III]

or a mixture thereof;

wherein R is a galloyl group represented by the following Formula A:

[Formula A]

(A)

5. The method according to claim 4 wherein the composition is a food or drink.

6. The method according to claim 5 wherein the food or drink is a tea beverage.

* * * * *